(12) United States Patent
Beckett

(10) Patent No.: US 9,392,826 B2
(45) Date of Patent: Jul. 19, 2016

(54) FALL DETECTION AND HIP IMPACT PROTECTOR

(75) Inventor: William E. Beckett, London (GB)

(73) Assignee: Fall-Safe Assist Ltd., Oxon (GB)

( * ) Notice: Subject to any disclaimer, the term of this patent is extended or adjusted under 35 U.S.C. 154(b) by 59 days.

(21) Appl. No.: 14/123,167

(22) PCT Filed: May 25, 2012

(86) PCT No.: PCT/GB2012/051184
§ 371 (c)(1),
(2), (4) Date: Dec. 27, 2013

(87) PCT Pub. No.: WO2012/164265
PCT Pub. Date: Dec. 6, 2012

(65) Prior Publication Data
US 2014/0111339 A1    Apr. 24, 2014

(30) Foreign Application Priority Data

Jun. 1, 2011   (GB) .................................. 1109170.9

(51) Int. Cl.
*G08B 23/00*   (2006.01)
*A41D 13/05*   (2006.01)
(Continued)

(52) U.S. Cl.
CPC .......... *A41D 13/0506* (2013.01); *A61B 5/1117* (2013.01); *G08B 21/043* (2013.01); *G08B 21/0446* (2013.01); *A61B 5/1112* (2013.01); *A61B 2503/08* (2013.01); *A61B 2505/07* (2013.01); *A61B 2562/0219* (2013.01); *A61B 2562/0252* (2013.01); *A61B 2562/187* (2013.01)

(58) Field of Classification Search
CPC .......... A41D 13/0506; G08B 21/0446; A61B 2503/08; A61B 2505/07
See application file for complete search history.

(56) References Cited

U.S. PATENT DOCUMENTS

2004/0003455 A1   1/2004 Davidson
2004/0209600 A1*  10/2004 Werner et al. .............. 455/414.1
(Continued)

FOREIGN PATENT DOCUMENTS

GB    2 323 196 A    12/1998
TW    200906369 A    2/2009
(Continued)

OTHER PUBLICATIONS

International Search Report and Written Opinion from corresponding International Application No. PCT/GB2012/051184, dated Aug. 16, 2012.
(Continued)

*Primary Examiner* — Omeed Alizada
(74) *Attorney, Agent, or Firm* — Renner, Otto, Boisselle & Sklar, LLP

(57) ABSTRACT

This invention relates to hip protector devices. We describe a hip protector for protecting a user in the event of a fall, the hip protector comprising: one or more hip protection elements; and an electronic fall detection system, wherein the hip protection element is arranged to reduce the impact of a fall by a user; wherein the fall detection system is configured to detect the occurrence of said fall by said user and to store fall data defining one or more characteristics of said detected fall in a data store, for later retrieval; wherein said hip protection element comprises a cushion or pad, and wherein said electronic fall detection system is located within said cushion or pad.

19 Claims, 2 Drawing Sheets

(51) Int. Cl.
*G08B 21/04* (2006.01)
*A61B 5/11* (2006.01)

(56) References Cited

U.S. PATENT DOCUMENTS

| | | | |
|---|---|---|---|
| 2005/0169439 A1* | 8/2005 | Binning | 379/45 |
| 2006/0059400 A1* | 3/2006 | Clark et al. | 714/752 |
| 2006/0214806 A1 | 9/2006 | Clifford | |
| 2008/0117060 A1 | 5/2008 | Cuddihy et al. | |
| 2008/0133277 A1 | 6/2008 | Jang et al. | |
| 2009/0076419 A1 | 3/2009 | Namineni et al. | |
| 2011/0090079 A1* | 4/2011 | Morino et al. | 340/532 |
| 2012/0101411 A1* | 4/2012 | Hausdorff et al. | 600/595 |
| 2013/0192336 A1* | 8/2013 | O'Connor | 73/12.01 |

FOREIGN PATENT DOCUMENTS

| | | |
|---|---|---|
| WO | WO 2010/004538 A1 | 1/2010 |
| WO | 2010/023604 A1 | 3/2010 |
| WO | 2011/043675 A1 | 4/2011 |
| WO | 2011/055255 A1 | 5/2011 |

OTHER PUBLICATIONS

UK Search Report dated May 1, 2012 for corresponding UK Application No. GB1109170.9.
UK Examination Report dated Jul. 30, 2013 for corresponding UK Application No. GB1109170.9.

* cited by examiner

FALL DETECTION AND HIP IMPACT PROTECTOR

FIELD OF THE INVENTION

This invention relates to hip protector devices.

BACKGROUND TO THE INVENTION

Hip protectors are devices used to protect a wearer's hip in the event of a fall. They typically have a padded region located about the hip region of a person in order to reduce the impact of a fall. Hip protectors come in different forms, including underwear with integrated hip protector pads, trousers with integrated hip protectors or pockets positioned for removable hip protectors.

The use of hip protector devices is important in the prevention of hip fractures. They can be an important aid to people more prone to falling over, such as the elderly, or to those suffering from osteoporosis. Furthermore, following a hip operation, it can be desirable to provide increased protection of the hip region during recovery.

In the event of a fall that does result in injury, it can be difficult (sometimes impossible) for the injured person to seek help, especially if the injured person is alone at the time of the accident.

Furthermore, it can also prove difficult to assess the severity of a fall and if a person is frail or confused, they may not be able to recollect what happened or remember when the fall occurred.

There is therefore need for an improved hip protector that can address such problems.

SUMMARY OF THE INVENTION

According to a first aspect of the invention there is provided a hip protector for protecting a user in the event of a fall, the hip protector comprising: one or more hip protection elements; and an electronic fall detection system, wherein the hip protection element is arranged to reduce the impact of a fall by a user; and wherein the fall detection system is configured to detect the occurrence of the fall by the user and to store fall data defining one or more characteristics of the detected fall in a data store, for later retrieval.

The hip protector is able to protect a user in the event of a fall should a user accidentally fall over, reducing the impact on a user's hip. The hip protector also comprises an electronic fall detection system to detect any occurrences of a fall for subsequent analysis and review by the user's GP or carer.

The hip protector comprises a cushion or pad, and the electronic fall detection system is located within the cushion or pad. In other words, the fall detection system is fitted within the hip protection element for ease of use by the wearer. In such an arrangement the fall detection system may be sufficiently small such that it does not affect the performance of the hip protection element, i.e. it does not impose on the user in the event of a fall when the hip protection element may compress or deform.

The hip protector incorporates the fall detection system within the hip protector itself. This makes it practical to wash or tumble dry the pants without damaging the fall detection system, and protects the system when the pants are put on or taken off, and in a fall. In this way, embodiments of the hip protectors may last for several years.

The fall characteristics stored in the fall data may comprise one or more of impact data defining the impact intensity of a user's fall; direction data defining a direction of the fall; and timestamp data defining at least one of a time and date of the fall. Such data may be used to support the assessment of the user's wellbeing and can be analysed by a carer or GP to ensure that the user is safely mobile. If a person is unable to recover from a fall, the data can also be used to determine how long the user has been immobile. Such data can be particular useful where the person is dazed or confused following the fall and is unable to recite the events clearly.

The fall detection system may include a fall sensor to generate movement data for detecting the fall occurrence. The fall sensor may comprise an accelerometer to generate movement data for detecting the occurrence of a fall. To detect changes of motion in all directions a three axis accelerometer or preferably one or more gyroscopes—which generate movement direction data—may also be used. Additionally or alternatively, a switch may be provided, which activates on pressure against the floor in the event of fall. Additionally one or more load cells may be incorporated in the hip protector to measure the force of the fall. A tilt switch, such as a mercury tilt switch may also be used to generate movement data, and in embodiments with multiple tilt switches, even movement direction data, in the event of a user changing from a upright position to a lying position (such as by the result of a fall). Thus additionally or alternatively the fall sensor may comprise one or more tilt switches.

It can be important for the institution caring for the patient, or for carers at home, to know the direction of the fall so that trip or slip hazards can be removed/remedied. For example a fall forward can be due to a trip, and a slip backwards could be because of liquid on the floor.

The fall detection system may further comprise a processing element. The processing element may be configured to process the movement data generated from the fall sensor to detect the occurrence of a fall and output the fall data. The processing element may then store the generated fall data in the data store.

In other words, the processing element is configured to read data from the fall sensor (such as an accelerometer, gyroscope, and/or load cell) and determine if the user has fallen over, storing any output data relating to the fall in the data store such that the fall event is logged for subsequent analysis.

The fall detection system may further comprise a data logging communications link coupled to the processing element. The data logging communications link may be configured to communicate the fall data to a data logger for downloading a history of detected falls and characteristics of such falls.

The link to the data logger may be wired or wireless. For ease of use, a wireless link is preferred, but not essential. A wireless link may comprise a Bluetooth wireless link for example.

The data logger, which may be a dedicated device or conventional computer may receive data from the fall detector over the wired or wireless link. The data may then be stored for subsequent review/analysis. If a user is resident in a nursing home or hospital, the data logger may be configured to receive data from multiple users.

The fall detection system may be configured to automatically communicate the fall data stored in the data store to the data logger via the data logging communications link when a connection between the fall detector and the data logger is established. In other words, when the fall detector and data logger come within range of one another, the data may be automatically transferred without any intervention by the user. In variants, a connection may need to be manually established, and then the data may be automatically transferred.

In some systems the data store may comprise a removable memory card, thus although a data logging communications link may be present, an alternative way of transferring the fall data to the data logger is by removing the memory card from the fall detector and inserting it into the data logger/computer.

In the event of a fall, the processing element in the fall detection system may be configured to monitor the movement data for a predetermined time period to provide an assessment of the mobility of the user. If a threshold level of movement has not been exceeded within a predetermined time, or the movement data is suggestive that the user is distressed (such as lying horizontally following a fall event), it may be that the user is unable to move (they may be unconscious or injured). An alarm signal may be generated by the fall detection system for alerting a third party that the person is in distress.

The alarm event may be communicated to a third party using an emergency communications link which may connect to established personal distress systems, such as those connected to telephone lines to signal a family member, carer or member of the emergency services. The alarm signal data may comprise some or all of the fall data and/or may further comprise identification data identifying the user or fall detection system (from which a user may be subsequently determined if the fall detector has been registered). Preferably the emergency communications link on the hip protector system is wireless.

Some variants of the hip protector may further comprise a location detector, such as a GPS receiver, to determine the location of the hip protector (and thus, the user wearing the hip protector). Should a user fall, then the location data may also be stored in the data store in order to assess any particular locations that may be problematic for the user. It will be appreciated however that other forms of location detecting systems, in addition to GPS are possible and other systems may allow for improved usage indoors.

In the event of a fall that generates alarm data signalling that the user may be in distress, then the location data may be transmitted as part of the alarm event to provide a location of the user to the recipient party.

The hip protection element may comprise a deformable region which helps to absorb the impact such a user fall.

In some embodiments the fall detector may be removable from the hip protection element such that the hip protection element can be washed and dried. Furthermore this also allows the user to swap and change hip protection elements, but maintain use of the fall detector which may have been preconfigured to an individual user. In preferred embodiments, however, the fall detector comprising flexible circuit board mountings, and is sealed into a waterproof capsule within the hip protector to prevent damage. The battery is charged by an inductive charging system so that it need not be removed nor connected to a charger with a cable.

According to a second aspect of the invention there is provided a hip protector for protecting a user in the event of a fall, the hip protector comprising: one or more hip protection elements; and an electronic fall detection system, wherein the hip protection element is arranged to reduce the impact of a fall by a user; and wherein the fall detection system includes an accelerometer to generate movement data for detecting an occurrence of the fall by the user, wherein the fall detection system further includes one or more gyroscopes to detect the direction of fall by the user, wherein responsive to detecting the fall occurrence the fall detection system is configured to monitor the movement data for a predetermined time period, and responsive to the fall detection system determining from the movement data that the user is immobile, the fall detection system is configured to generate an alarm signal for alerting a third party.

Thus, the hip protector is able to alert a third party in the event of a fall and, importantly to determine the fall direction using the gyroscope(s) (which may be MEMS gyroscope(s)). This may be performed using a fall sensor and communicated using any of the features previously described.

According to a further aspect of the invention there is provided a method of monitoring falls of an elderly or infirm person, the method comprising: incorporating an electronic fall detection system in a hip protector; monitoring one or more of a fall time, a fall force and a fall direction of the person using the electronic fall detection system; and performing one or both of: storing the fall time, and the fall force, and/or fall direction for later interrogation; and generating an alarm responsive to one or more of the fall time, fall force, fall direction and a detected duration of immobility of the person after a said fall.

The electronic fall detection system may comprise any of the features previously described. Fall time, force and/or direction may be monitored and can be useful information for a carer or medic treating the person in order to understand how and when the person fell. An alarm may also be signalled in the event of a fall, dependent on fall characteristics including time, force, direction and a duration the person has been immobile for.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENTS

Figure 1:
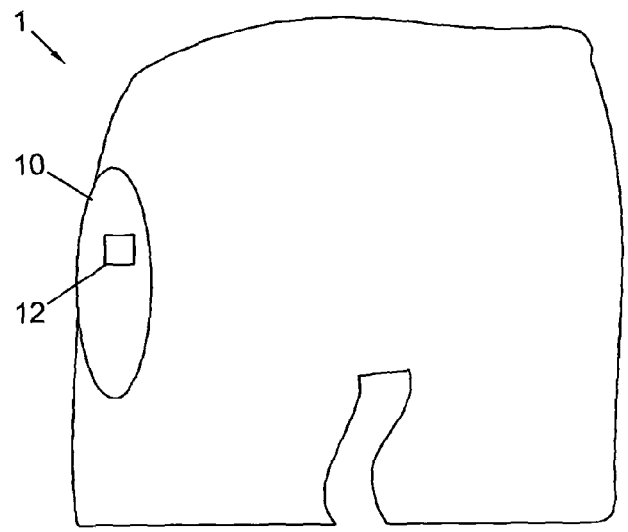
FIG. 1 shows an embodiment of the hip protector with the implanted fall detector.

FIG. 1 shows the hip protector 1. The hip protector has a fall detector 12 (a Fall-Safe® Assist) implanted in a hip protector pad or element 10, such as a Fall-Safe® hip protector. In FIG. 1, the fall detector is an integral part of the hip protector to minimise any awkwardness for the user. The hip protector pad/element shown in FIG. 1 comprises foam, but any other type of deformable structure such as foam and the like may also be used to absorb the impact of a fall.

In variants the fall detector is removable from the hip protector to allow the hip protector to be washed and to allow the fall detector to be used interchangeably between multiple hip protector pads by a user. This allows a fall detector to be preconfigured for a particular user, including data such as identification data and any further customisations that may be needed.

Figure 2:
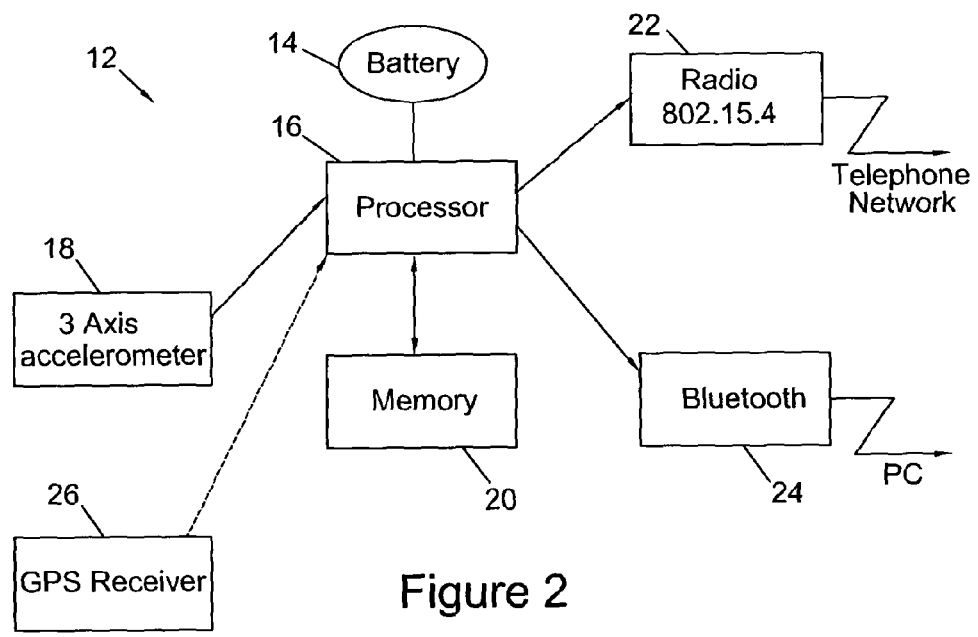
FIG. 2 shows the internal structure of the fall detector of FIG. 1.

FIG. 2 shows an example of the internal arrangement of a fall detector 12. The fall detector monitors for and identifies the following:
  When a fall occurs;
  The force of a fall, i.e. how hard the person hits the floor or ground; and
  The direction that the wearer fell, i.e. forwards, backwards, on left side or right hand side.

A three axis accelerometer 18, shown in FIG. 2, is used to detect a fall. Data is processed using processor 16 and can be stored in memory 20. In the embodiment shown in FIG. 2 the processor and memory may are part of a small microcontroller device or a PIC type device and integrated onto the same chip. Such devices have further components, such as a real time clock and timers which are usable by the fall detector device as described later.

In variants of the system the memory may be removable, provided by a memory card such as a micro-SD card.

When a person wearing the device passes within range of a wireless connection previously stored data, such as data from prior falls is automatically transferred from the hip protector to minimise the data stored locally to the device. This data may be used for analysis by an institution such as a hospital or care/nursing home, or by the person's GP. It could also be used to improve nursing care and identify hazards.

In the example embodiment shown in FIG. 2 a Bluetooth chipset 24 is used to provide a Bluetooth wireless connection for data download to a PC or other form of data logger. It will be appreciated however that other forms of wireless connection may also be used, such as Wifi or Zigbee (or in some variants a wired connection may be necessary in order to reduce costs). With a device powered by battery 14 it will be desirable to minimise power consumption and therefore choosing a low powered wireless connection is preferable.

In addition to the data download connection provided by the Bluetooth chipset 24, it may be desirable to include a further wireless connection for emergency purposes.

If a person does not move for a predetermined number of seconds after a fall, then an emergency signal can be sent via Bluetooth™ to a local radio controller or mobile phone device in the same building. This may then connect to a phone line to call a remote alarm centre or the 24-hour nursing station in a hospital or care home.

The data transmitted may include all or part of the data transmittable over the Bluetooth connection and may also include some or all of the customisable information stored such as identification data.

This time lapse before triggering an alarm may be adjustable in the light of experience and the individual's circumstances.

It will be appreciated however that in some variants of the system the two wireless connections could be combined in order to reduce the number of wireless transmitters on the fall detector.

In a modified version of the fall detector, a GPS receiver 26 may be provided. This may be integral to the fall detector or alternatively could be an independent device with a connection to the fall detector. Should a person fall outdoors (where a GPS signal is typically stronger allowing location to be determined), location data from the GPS receiver may be transmitted with the other detector data as part of an alarm/emergency call.

The location data may also be logged to help identify areas more problematic for the wearer.

Figure 3:
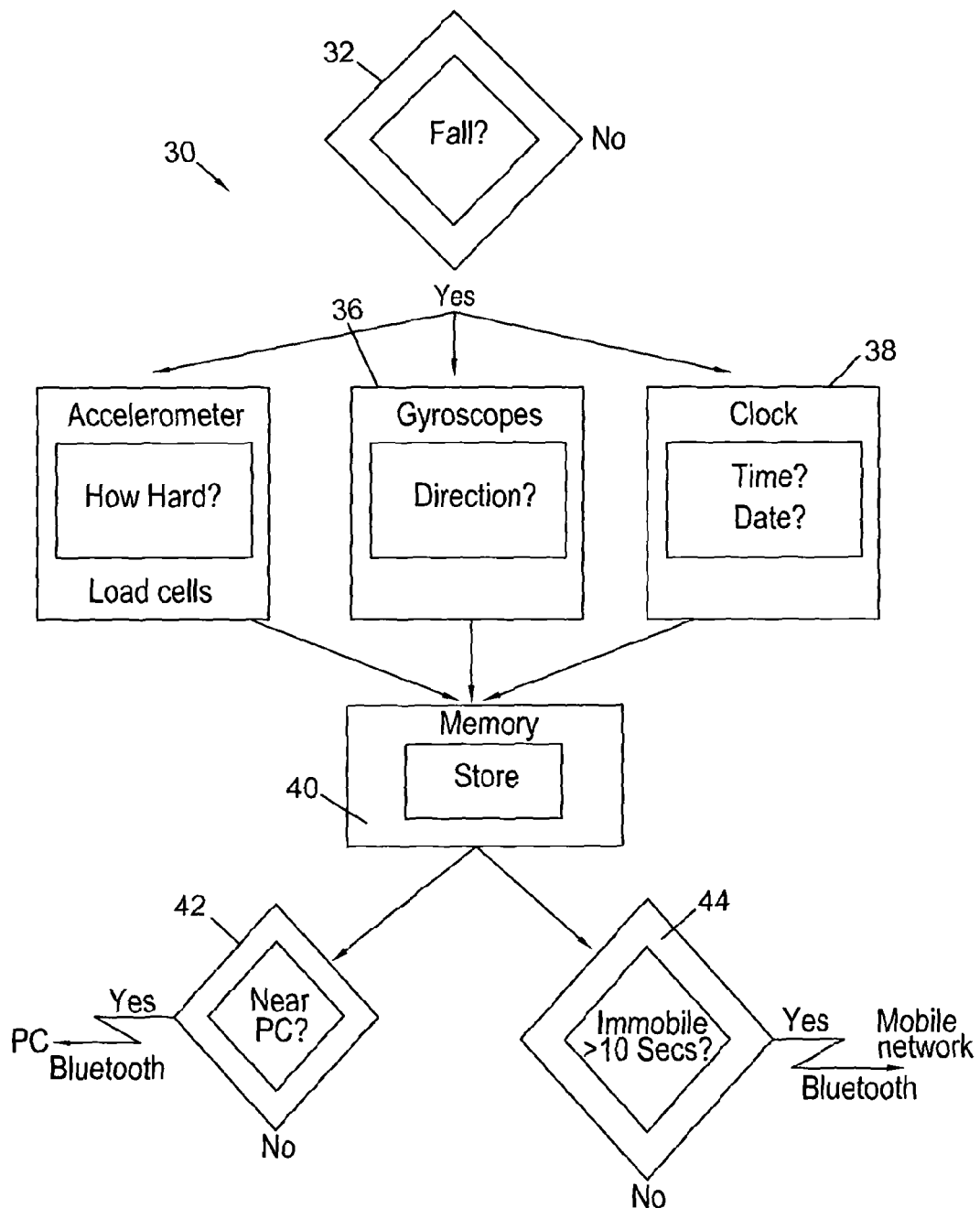
FIG. 3 shows a flow chart summarising the series of steps performed by the fall monitor chip.

FIG. 3 shows a flow chart 30 defining an example process implemented within the fall detector of FIG. 2.

A fall is detected at step 32 using data from the accelerometer 18. Data from the accelerometer is used by the processor 16 to determine characteristics of the fall such as intensity at step 34. This is complemented by data acquired from one or more load cells, also in embodiments at step 34 if the user falls onto the hip, as opposed to any other part of the body.

One or more gyroscopes provide data on the direction of the fall at step 36. At step 38 further data relating to the time and/or date of the fall is recorded. Such data may be provided by a real time clock integrated onto a microcontroller or PIC type device used to provide the processor 16. The data generated is then stored in memory 40.

Data transfer takes place at step 42. This may happen automatically when a user comes within proximity of a computer/data logger type of device. Alternatively, in simpler systems, it may be necessary for the user to initiate the connection to the fall detector to the computer/data logger and manually download the data using a wireless or wired connection (such as USB). In variants where a removable memory card is used, another option is for a user to remove the card from the hip protector fall detector and insert it into the computer/data logger.

Having detected a fall, a timer may be triggered on the fall detector at step 44 to subsequently active an alarm if the person fails to move again within a predetermined time (which may be customisable). An example shown in FIG. 3 is a trigger time of 10 seconds, although it will be appreciated that this may be varied depending on the person's circumstance. Such a time may be set by the user, or alternatively may be set by a carer or GP.

Because a fall detection system may be incorporated into each of the two hip protectors that the user wears, if one device fails or is damaged then the other may capture the fall data and send alarms if required. Additionally, if one device is providing inaccurate or spurious data, the software program in the other fall detector may detect that this is occurring and signal an error condition to the computer/data logger.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A hip protector for protecting a user in the event of a fall, the hip protector comprising:
   one or more a pair of hip protection elements; and
   wherein each of said hip protection elements incorporates an electronic fall detection system comprising one or both of an accelerometer to generate movement data and a gyroscope to generate movement direction data;
   wherein the hip protection elements are arranged to reduce the impact of a fall by a user;
   wherein the fall detection systems are configured to detect the occurrence of said fall by said user and to store fall data defining one or more characteristics of said detected fall in a data store, for later retrieval;
   wherein a said hip protection element comprises a cushion or pad; and
   wherein a said electronic fall detection system is located within a said cushion or pad;
   wherein the respective said fall detection systems are in communication with one another; and
   wherein a said fall detection system is configured to detect inaccurate or spurious data of said movement data and movement direction data being provided by the other said fall detection system due to a fault or error condition in said other fall detection system.

2. A hip protector as claimed in claim 1, wherein a said fall detection system includes a load sensor within said cushion or pad to detect a severity of an impact of said fall.

3. A hip protector as claimed in claim 2, wherein said load sensor comprises one or more load cells.

4. A hip protector as claimed in claim 2, wherein said characteristics of said detected fall comprise impact data defining the impact intensity of said fall.

5. A hip protector as claimed in claim 1, wherein said characteristics of said detected fall comprise timestamp data defining at least one of a time and date of said fall.

6. A hip protector as claimed in claim 1, wherein a said fall detection system comprises a processing element, and
    wherein said processing element is configured to process said movement data to detect said fall occurrence and output said fall data, and
    wherein said processing element is further configured to store said fall data in said data store.

7. A hip protector as claimed in claim 6, wherein a said fall detection system further comprises a data logging communications link coupled to said processing element, and
    wherein said processing element is configured to communicate said fall data to a data logger via said data logging communications link.

8. A hip protector as claimed in claim 6, wherein responsive to detecting said fall occurrence said processing element is configured to monitor said movement data for a predetermined time period, and
    responsive to said processor determining from said movement data that said user is immobile, said processing element is configured to generate an alarm signal for alerting a third party.

9. A hip protector as claimed in claim 8 wherein said determining from said movement data that said user is immobile comprises determining if a threshold level of movement has not been exceeded.

10. A hip protector as claimed in claim 8, wherein a said fall detection system is configured to communicate said alarm signal to a remote party using an emergency communications link.

11. A hip protector as claimed in claim 10, wherein said emergency communications link comprises a wireless communications link.

12. A hip protector as claimed in claim 7, wherein a said fall detection system is configured to automatically communicate said fall data to said data logger via said data logging communications link when a connection between said fall detection system and said data logger is established.

13. A hip protector as claimed in claim 7, wherein said data logging communications link comprises a wireless communications link.

14. A hip protector as claimed in claim 1, wherein said data store comprises a removable memory card.

15. A hip protector as claimed in claim 1, further comprising a location detector to determine a location of said hip protector, and
    wherein responsive to detecting a fall, a said fall detection system is further configured to store said determined location in said data store.

16. A hip protector as claimed in claim 10, further comprising a location detector to determine a location of said hip protector,
    wherein responsive to detecting a fall, a said fall detection system is further configured to store said determined location in said data store, and
    wherein said alarm event comprises data defining said determined location.

17. A hip protector as claimed in claim 1, wherein a said fall detection system is removable from said hip protection element.

18. A hip protector as claimed in claim 1, wherein a said fall detection system includes a rechargeable power source and an inductive charging system to enable remote wireless charging of said rechargeable power source.

19. A method of monitoring falls of an elderly or infirm person, the method comprising:
    incorporating an electronic fall detection system in each of a pair of hip protection elements of a hip protector, wherein a said electronic fall detection system comprises one or both of an accelerometer to generate movement data and a gyroscope to generate movement direction data;
    monitoring one or more of a fall time, a fall force and a fall direction of said person using a said electronic fall detection system; and
    performing one or both of:
    storing said fall time, said fall force and/or fall direction for later interrogation; and
    generating an alarm responsive to one or more of said fall time, fall force, fall direction and a detected duration of immobility of said person after a said fall;
    wherein the respective said fall detection systems are in communication with one another; and
    wherein a said fall detection system is configured to detect inaccurate or spurious data of said movement data and movement direction data being provided by the other said fall detection system due to a fault or error condition in said other fall detection system.

\* \* \* \* \*